United States Patent [19]

Kurosawa et al.

[11] Patent Number: 4,976,268
[45] Date of Patent: Dec. 11, 1990

[54] PRESSURE-PULSE-WAVE DETECTING APPARATUS

[75] Inventors: Kimimasa Kurosawa, Komaki; Chikao Harada, Nagoya; Hiroshi Sakai, Kasugai; Minoru Niwa, Nagoya, all of Japan

[73] Assignee: Colin Electronics Co., Ltd., Japan

[21] Appl. No.: 369,684

[22] Filed: Jun. 21, 1989

[30] Foreign Application Priority Data

Jun. 24, 1988 [JP] Japan .................. 63-157735

[51] Int. Cl.$^5$ .............................................. A61B 5/02
[52] U.S. Cl. ................................. 128/687; 128/633; 128/667
[58] Field of Search ............... 128/687, 689, 690, 691, 128/633, 748, 667, 666, 664, 665

[56] References Cited

U.S. PATENT DOCUMENTS

| | | | |
|---|---|---|---|
| 3,040,737 | 6/1962 | Kompelien et al. | 128/667 |
| 4,201,222 | 5/1980 | Haase | 128/667 |
| 4,210,029 | 7/1980 | Porter | 73/705 |
| 4,259,963 | 4/1981 | Huch | 128/666 |
| 4,269,193 | 5/1981 | Eckerle | 128/672 |
| 4,423,738 | 1/1984 | Newgard | 128/672 |
| 4,487,206 | 12/1984 | Aagard | 128/667 |
| 4,711,246 | 12/1987 | Alderson | 128/667 |
| 4,735,212 | 4/1988 | Cohen | 128/667 |
| 4,787,396 | 11/1988 | Pidorenko | 128/667 |
| 4,803,992 | 2/1989 | Lemelson | 128/667 |

FOREIGN PATENT DOCUMENTS 306394 10/1989 European Pat. Off. .
2132483 7/1984 United Kingdom ............. 128/691
2186360 8/1987 United Kingdom .

Primary Examiner—Lee S. Cohen
Assistant Examiner—Scott M. Getzow
Attorney, Agent, or Firm—Oliff & Berridge

[57] ABSTRACT

An apparatus for detecting pressure pulse wave, including a main body having a pressing surface which is pressed against the body surface of a subject, and a plurality of through holes formed therethrough and opening in the pressing surface; a plate member secured to the pressing surface of the main body such that the plate member covers the openings of the through holes, the pressing plate having flexibility and including a plurality of displaceable portions each of which is aligned with the opening of a corresponding through hole; a plurality of optical fibers, one of opposite ends of each optical fiber being fitted in a corresponding through hole of the main body, such that an end face of the one end is opposed to a corresponding displaceable portion of the plate member at a predetermined distance therefrom; and a plurality of signal generating devices each of which is connected to the other of the opposite ends of a corresponding optical fiber, each signal generating device detecting the pressure pulse wave transmitted to a corresponding displaceable portion of the plate member, based on minute displacement of the corresponding displaceable portion which is optically detected through the corresponding optical fiber, and generating an electric signal representing the detected pressure pulse wave.

10 Claims, 3 Drawing Sheets

AMPLITUDE
(PRESSURE)

TIME

PRESSURE-PULSE-WAVE DETECTING APPARATUS

BACKGROUND OF THE INVENTION

1. Field of the Art

The present invention relates to an apparatus for detecting pressure pulse wave produced from an arterial vessel of a living body, at a plurality of positions on a body surface right above the arterial vessel.

2. Related Art Statement

Pressure pulse wave produced from an artery of a living body in synchronization with pulsation of the heart, provides information on the cardiovascular system of the subject such as active condition of the heart, blood pressure and degree of arterial sclerosis. There is known a device which detects the pressure pulse wave produced from an artery of a subject, by using a pressure sensor which is pressed against the artery via the body surface right thereabove. However, the pressure sensor is adapted to contact at a pressing surface thereof the body surface over a whole width (or diameter) of the artery. In other words, the pressing surface of the pressure sensor is larger than the width of the artery. For this reason the detection of the pressure pulse wave may be adversely influenced by the wall of the artery, and the detected pressure pulse wave may not provide accurate information.

To overcome the above-indicated problem it has been proposed to detect pressure pulse wave at a plurality of positions which are spaced apart from each other on the body surface in a direction crossing the artery, by a length smaller than the width of the artery. An example of the pressure-pulse-wave detecting device of this type is disclosed by U.S. Pat. No. 4,423,738. The device disclosed therein is capable of selecting the single one of the plurality of positions which is substantially free from the problem of the wall of the artery and at which a blood pressure approximate to an intra-arterial blood pressure is measured.

Further, the assignee of the present application has filed Japanese Patent Application No. 63-87720 on Apr. 9, 1988, in which it is proposed to measure a degree of arterial sclerosis of an artery of a subject by detecting pressure pulse wave at a plurality of positions on the body surface right above the artery. Japanese Patent Application No. 63-87720 was published under Publication No. 1-359836 on Oct. 17, 1989.

In the above-indicated devices in which pressure pulse wave is detected at a plurality of positions on the body surface right above an artery, however, the number of the detecting positions was insufficiently low, in particular in the case of an artery of a comparatively small width. More specifically described, the pressure sensor employed in those devices consists of a semiconductor plate of a comparatively large thickness and a comparatively high rigidity. The semiconductor plate includes a plurality of pressure-receiving portions (i.e., pressure-detecting elements) of a comparatively small thickness which are provided by forming a plurality of recesses in one of opposite surfaces of the plate in a direction of thickness thereof by photoetching technique. Upon application of a pressure to the semiconductor plate, a strain is produced in the pressure-receiving portions. However, if each pair of adjacent recesses are formed excessively near to each other, it is not permitted to form an electrically conductive wiring pattern in an area between the each pair of recesses. Further, in such a case the rigidity of the semiconductor plate as a whole is disadvantageously lowered, and the accuracy of pressure measurement is sacrificed. Thus, the pressure-receiving portions of the semiconductor plate must be spaced apart from each other by a distance greater than a required minimum length.

SUMMARY OF THE INVENTION

It is therefore an object of the present invention to provide a pressure-pulse-wave detecting apparatus wherein pressure pulse wave is detected at an increased number of positions per unit distance on the body surface right above an artery, namely, by utilizing a high density of measuring points.

The above object has been achieved by the present invention, which provides a pressure-pulse-wave detecting apparatus for detecting pressure pulse wave produced from an arterial vessel of a subject, at a plurality of positions on a body surface right above the arterial vessel, the apparatus comprising: (a) a main body having a pressing surface which is pressed against the body surface, and a plurality of through holes formed therethrough and opening in the pressing surface; (b) a plate member secured to the pressing surface of the main body such that the plate member covers the openings of the plurality of through holes, the pressing plate having flexibility and including a plurality of displaceable portions each of which is aligned with the opening of a corresponding one of the plurality of through holes; (c) a plurality of optical fibers, one of opposite ends of each of the plurality of optical fibers being fitted in a corresponding one of the plurality of through holes of the main body, such that an end face of the one of opposite ends is opposed to a corresponding one of the plurality of displaceable portions of the plate member at a predetermined distance therefrom; and (d) a plurality of signal generating devices each of which is connected to the other of the opposite ends of a corresponding one of the plurality of optical fibers, the each signal generating device detecting the pressure pulse wave transmitted to a corresponding one of the plurality of displaceable portions of the plate member, based on minute displacement of the corresponding displaceable portion which is optically detected through the corresponding optical fiber, and generating an electric signal representing the detected pressure pulse wave.

In the pressure-pulse-wave detecting apparatus of the invention constructed as described above, the plate member with flexibility is secured to the pressing surface of the main body in which are open the plurality of through holes formed through the main body, and the plurality of optical fibers are connected to the main body such that each of the optical fibers is fitted at one of opposite ends thereof in a corresponding one of the through holes and that an end face of the one end of the each optical fiber is opposed to the plate member secured to the main body. With the plate member pressed against the body surface right above an arterial vessel of a subject, the displaceable portions of the plate member which are aligned with the corresponding through holes, minutely displace upon application of the pressure pulse wave thereto. The signal generating devices optically measure minute displacements of the displaceable portions of the plate member, through the optical fibers, and detect the pressure pulse wave based on the measured minute displacements of the plate member.

Thus, the main body used in the present apparatus does not require electrically conductive wiring patterns to be formed between the measuring points, specifically the through holes of the main body, in contrast to the conventional apparatus. Further, the thickness of the main body is not limited to not more than a certain value, namely, may be of a comparatively large thickness. Also, the main body may consist of a member having a comparatively high rigidity. Thus, the main body does not suffer from the problem of reduced rigidity, though the plurality of through holes are formed therethrough. Therefore, each pair of adjacent through holes are formed so as to be spaced apart from each other by a very small distance. Consequently the present apparatus is capable of detecting pressure pulse wave at a sufficiently large number of positions per unit distance on the body surface right above the artery, namely, by utilizing a sufficiently high density of measuring points.

According to a feature of the present invention, the apparatus further comprises pressing means for pressing the plate member secured to the pressing surface of the main body, against the body surface, the pressing means comprising a cylindrical housing with a bottom wall, for accommodating the main body; a flexible diaphragm disposed between the housing and the main body, for securing the main body to the housing, the diaphragm cooperating with the housing to define a fluid-tight pressure chamber; a band for setting the housing on the body surface; and a pressure source for supplying the pressure chamber with pressurized fluid so as to press the main body against the body surface.

According to another feature of the invention, the main body has rigidity.

According to yet another feature of the invention, the main body has grooves formed in the pressing surface thereof, the grooves being covered by the plate member secured to the pressing surface, the plurality of through holes communicating with the atmosphere via the grooves covered by the plate member.

According to a further feature of the invention, the plurality of through holes are formed through the main body such that the through holes are arranged in a row at regular intervals of distance. In this case, it is recommended that each of the regular intervals of distance be about 0.2 mm long. Also, in this case, it is preferred that, with the main body pressed against the body surface, 3 to 5 through holes out of the plurality of through holes are located right above the arterial vessel.

In a prefered embodiment of the apparatus of the invention, each of the signal generating devices comprises a laser source for emitting laser beams having a single wavelength; a first convex lens for forming the laser beams into parallel beams; a non-polar beam splitter for dividing the parallel beams into a first and a second beam, such that the beam splitter transmits the first beam and reflects the second beam; a second convex lens for permitting the first beam to be incident on an end face of the other of the opposite ends of a corresponding one of the plurality of optical fibers, the first beam being transmitted by the corresponding optical fiber, reflected by a corresponding one of the displaceable portions of the plate member, again transmitted by the corresponding optical fiber, and reflected by the non-polar beam splitter, the first beam being varied in phase due to the minute displacement of the corresponding displaceable portion; a reflector mirror for reflecting the second beam, the second beam reflected by the reflector mirror being transmitted by the non-polar beam splitter; a photosensor for detecting a mixture light consisting of the first beam reflected by the beam splitter and the second beam transmitted through the beam splitter; and a detector circuit for reading a variation in phase of the mixture light at regular minute intervals of time, and generating the electric signal based on the periodically obtained readings.

In another embodiment of the invention, the apparatus further comprises a control device for processing the electric signals supplied from the plurality of signal generating devices, selecting one of the electric signals which is free from influences of the wall of the arterial vessel, and monitoring blood pressure of the subject based on the selected electric signal.

In yet another embodiment of the invention, the apparatus further comprises a control device for receiving the electric signals from the plurality of signal generating devices while varying the pressing force with which the main body is pressed against the body surface, and determining a degree of arterial sclerosis of the arterial vessel based on the received electric signals.

BRIEF DESCRIPTION OF THE DRAWINGS

The above and optional objects, features and advantages of the present invention will be better understood by reading the following detailed description of the presently preferred embodiment of the invention, when considered in conjunction with the accompanying drawings, in which.

DETAILED DESCRIPTION OF THE PREFERRED EMBODIMENT

Figure 1:
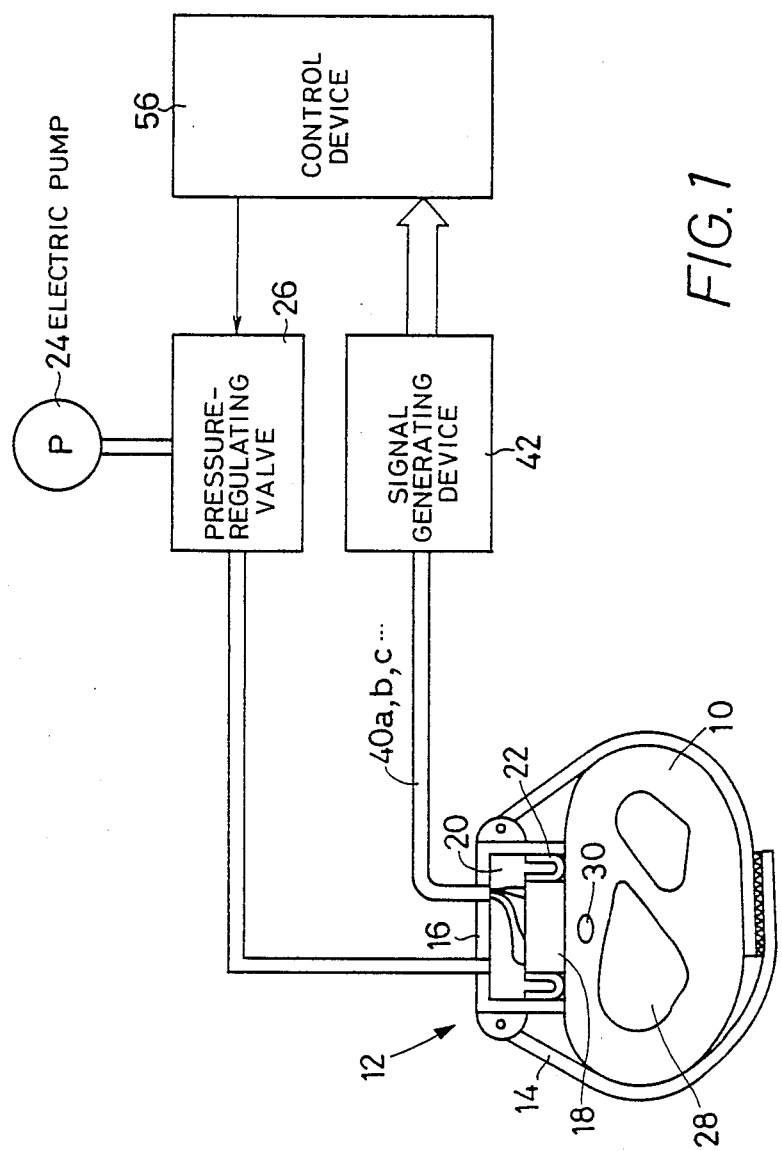
FIG. 1 is an illustrative view of a general arrangement of the pressure-pulse-wave detecting apparatus of the present invention.

Referring to FIG. 1 there is illustrated a general arrangement of a pressure-pulse-wave detecting apparatus of the present invention. In the figure, reference numeral 12 designates a detector head which is detachably fixed on a surface of a wrist 10 of a subject with the help of a wrist band 14. The detector head 12 includes a cylindrical housing 16 having a bottom wall, a main body 18 accommodated in the housing 16, and a flexible diaphragm 22 disposed between the housing 16 and the main body 18 for securing the main body 18 to the housing 16. The flexible diaphragm 22 cooperates with the housing 16 to define a fluid-tight pressure chamber 20. When pressurized gas is supplied from an electric pump 24 to the pressure chamber 20 via a pressure-regulating valve 26, the main body 18 is pressed via the body surface against a radial artery 30 running adjacent to a radius 28. Thus, the housing 16, diaphragm 22, band 14, pump 24 and other members cooperate with each other to serve as pressing means for pressing the main body 18 against the radial artery 30.

Figure 2:
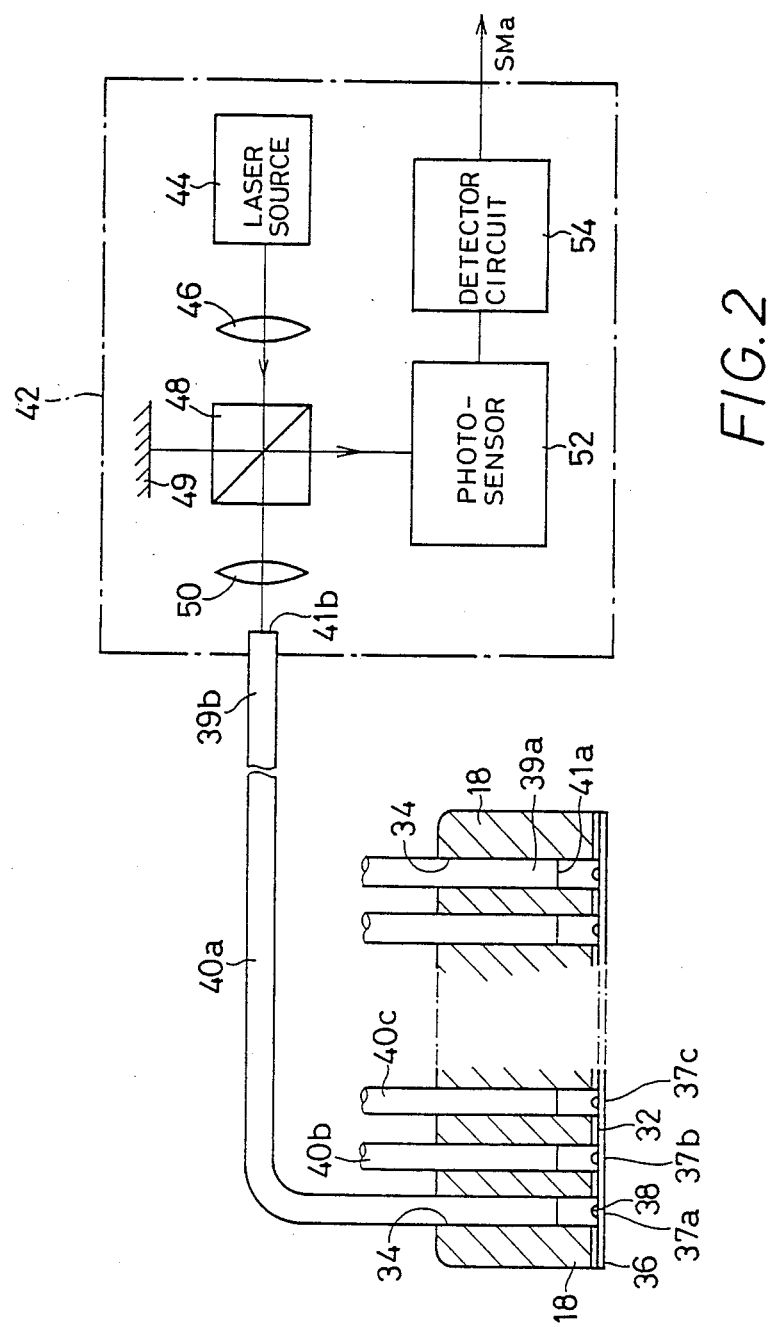
FIG. 2 is an illustrative view of a detector head and a signal generating device of the apparatus of FIG. 1.
Figure 3:
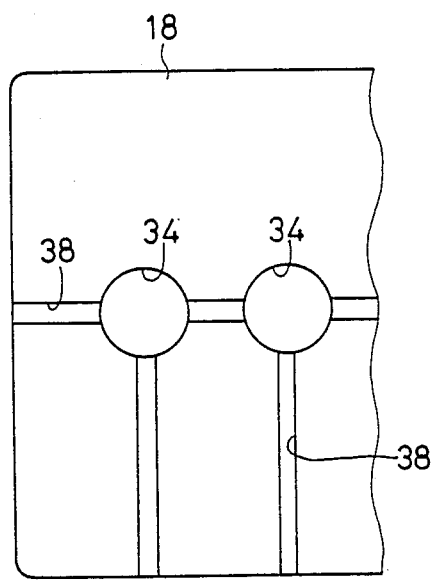
FIG. 3 is a view of a pressing surface of a main body accommodated in the detector head of the apparatus of FIG. 1.

The main body 18 consists of a member having a comparatively high rigidity, such as a metallic or ceramic member, and has a thickness of 2 to 20 mm. As shown in FIGS. 2 and 3, the main body 18 has a plurality of through holes 34 formed therethrough to open in a pressing surface 32 of the main body 18 and to be in a row along a predetermined straight line. A presser plate 36 is bonded to the pressing surface 32 of the main body 18 such that the presser plate 36 covers the through holes 34 opening in the pressing surface 32. The presser plate 36 is constituted by, for example, a glossy plated metal sheet of a comparatively small thickness, or a stainless-steel sheet of a comparatively small thickness, so that the presser plate 36 has a certain degree of flexibility. As most clearly shown in FIG. 3, the pressing surface 32 of the main body 18 has grooves 38 formed therein which are covered by the presser plate 36 secured to the pressing surface 32. The through holes 34 communicate with the atmosphere or ambient air via the grooves 38 covered by the presser plate 36, so as to prevent a pressure difference between the through holes 34 and the atmosphere. The plurality of through holes 34 are formed at regular intervals of distance. The distance intervals of the through holes 34 correspond to intervals of distance between the detecting positions at which pressure pulse wave produced from the radial artery 30 is detected. The distance intervals of the through holes 34 are predetermined to be sufficiently smaller than a width or diameter of the radial artery 30, for example about 0.2 mm, so that 3 to 5 through holes 34, and accordingly the same number of detecting positions, are located on the body surface right above the radial artery 30.

As shown in FIG. 2, a plurality of optical fibers 40a, 40b, 40c, . . . are connected to the main body 18 such that one end 39a of opposite ends 39a, 39b of each optical fiber 40 is fitted in a corresponding one of the plurality of through holes 34, and that an end face 41a of the one end 39a is opposed to or faces the presser plate 36 at a predetermined distance therefrom. The other end 39b of each optical fiber 40 is connected to a signal generating device 42. Accordingly, the instant apparatus includes a plurality of signal generating devices 42 whose number corresponds to that of the through holes 34. All of the devices 42 have the same configuration and operate in the same way.

There will be described in detail the signal generating device 42 connected to the optical fiber 40a. The signal generating device 42 includes a laser source 44 which emits laser beams having a single wavelength; a first convex lens 46 which forms the laser beams emitted by the laser source 44, into parallel beams; and a non-polar beam splitter 48 which divides the parallel beams into a first and a second beam such that the beam splitter 48 transmits the first beam and reflects the second beam. The signal generating device 42 further includes a reflector mirror 49 which reflects the second beam reflected by the beam splitter 48; and a second convex lens 50 which permits the first beam transmitted through the beam splitter 48 to be incident on an end face 41b of the other end 39b of the optical fiber 40a. The second beam reflected by the reflector mirror 49 is incident on the beam splitter 48. The first beam is transmitted by the optical fiber 40a which acts as a rod lens, reflected by the presser plate 36, again transmitted by the optical fiber 40a and is incident on the beam splitter 48. The signal generating device 42 also includes a photosensor 52 which receives a mixture light consisting of the second beam transmitted through the beam splitter 48 and the first beam reflected by the beam splitter 48, and generates an electric signal representing the detected mixture light; and a detector circuit which generates a pressure-pulse-wave electric signal SMa (hereinafter, referred to as PPW signal SMa) based on the electric signal supplied from the photosensor 52.

Figure 4:
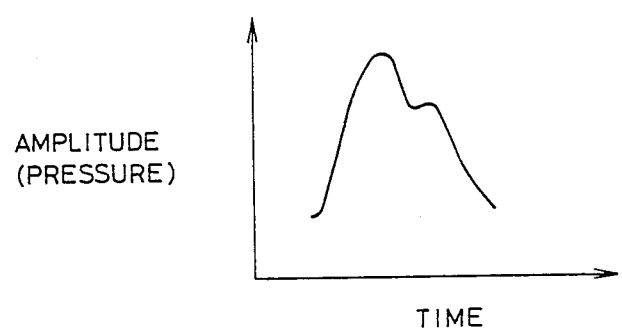
FIG. 4 is a view of a graph showing a cycle of pressure pulse wave represented by an electric signal generated by the signal generating device of FIG. 2.

More specifically described, PPW signal SMa generated by the detector circuit 54 of the signal generating device 42 connected to the optical fiber 40a, represents the pressure pulse wave transmitted to a displaceable portion 37a of the presser plate 36 which portion is aligned with the opening of the corresponding through hole 34 and is opposed to the end face 41a of the one end 39a of the optical fiber 40a. As described above, the mixture light detected by the photosensor 52, consists of the first beam reflected by the presser plate 36 and the second beam reflected by the reflector mirror 49. Upon application of pressure pulse wave from the radial artery 30 to the displaceable portion 37a of the presser plate 36, the displaceable portion 37a minutely displaces due to its flexibility, resulting in changing the optical path of the first beam and thereby varying the phase of the first beam. The optical path of the second beam is not changed, and the second beam is used as a reference light having a reference phase. The detector circuit 54 reads a shift of the phase of the first beam with respect to the reference phase of the second beam, which shift corresponds to a minute displacement of the presser plate 36, at regular minute intervals of time, and generates PPW signal SMa based on the periodically read shifts. Thus, PPW signal SMa represents the pressure pulse wave continuously acting on the displaceable portion 37a of the presser plate 36 in synchronization with pulsation of the heart of the subject. In the graph of FIG. 4 there is shown a cycle of the pressure pulse wave represented by PPW signal SMa, which corresponds to one pulsation of the heart.

The instant pressure-pulse-wave detecting apparatus further has a control device 56 which receives PPW signals SMa, SMb, SMc, . . . from the respective signal generating devices 42 connected to the respective optical fibers 40a, 40b 40c, . . . . . Each of PPW signals SMa, SMb, SMc, . . . represents the pressure pulse wave transmitted to a corresponding one of the displaceable portions 37a, 37b, 37c, . . . of the presser plate 36, namely, the pressure pulse wave detected at a corresponding one of the plurality of positions on the body surface right above the radial artery 30. The control device 56 processes the received PPW signals SMa, SMb, SMc, . . . according to software programs pre-stored therein, so as to select the single one of PPW signals, or the single one of the detecting positions, which is free from influences of the wall of the radial artery 30, as is taught by the previously indicated U.S. Pat. No. 4,423,738. The control device 56 monitors blood pressure of the subject based on the selected one PPW signal SM. Alternatively, the control device 56 may be adapted to receive PPW signals SM from the signal generating devices 42 while varying the pressing force with which the main body 18 is pressed against the radial artery 30, by controlling the pressuring-regulating valve 26, so as to determine a degree of arterial sclerosis of the radial artery 30 based on the received PPW signals SM, as taught by the previously indicated Japanese Patent Application No. 63-87720. In either case, the control device 56 commands a display (not shown) to display the measured blood pressure or degree of sclerosis of the subject.

It follows from the foregoing that in the instant apparatus it is not required to provide the plurality of through holes 34 with electrically conductive wiring patterns, in contrast to the conventional apparatus in which electrically conductive wiring patterns are provided between individual pressure-sensitive elements. Further, the main body 18 is free from limitation regarding thickness thereof. Also, as previously described, the main body 18 consists of a comparatively rigid member. Therefore, the rigidity of the main body 18 is not significantly reduced, even with the through holes 34 formed therethrough. Consequently, the through holes 34 are formed very near to each other. That is, the instant apparatus is capable of measuring the pressure pulse wave at a sufficiently large number of detecting positions per unit distance on the body surface right above the radial artery 30, namely by utilizing a sufficiently high density of detecting points.

The instant apparatus has no electric circuit in any parts thereof which directly contant the body surface of the subject, thereby ensuring use thereof with a higher safety.

While the presently preferred embodiment of the invention has been described with particularities for illustrative purpose only, it is understood that the present invention is not limited to the details of the illustrated embodiment but may be otherwise embodied.

For example, in place of the single presser plate 36 used in the illustrated embodiment, it is possible to use a plurality of separate displaceable or deformable members which are fitted in the openings of the correponding through holes 34.

While in the illustrated embodiment the main body 18 is moved with the diaphragm 22 expanded toward the wrist surface or radial artery 30, it is possible to further employ a device for moving the main body 18 in a direction crossing the radial artery 30, or a device for angularly positioning the main body 18 about an axis extending parallel to the radial artery 30.

Although in the illustrated embodiment each of the optical fibers 40a, 40b, 40c, ... consists of a single fiber, it is possible to use a bundle of fibers in place of the single fiber.

While in the illustrated embodiment pressure pulse wave is detected based on variation in the phase of the mixture light received by the photosensor 52, it is possible to detect the pressure pulse wave based on variation in amount or intensity of the light reflected by the presser plate 36. In this case it is preferred that at least one central optical fiber from which light is emitted toward the presser plate 36, and a bundle of outer optical fibers surrounding the at least one central fiber, for receiving the light reflected by the presser plate 36, be associated with each detecting position on the body surface right above the radial artery 30. The light transmitted by the bundle of outer optical fibers is received by a photosensor, which generates a PPW signal based on the received light. It is required that the light emitted toward the presser plate 36 is of a constant intensity or energy. As long as this requirement is satisfied, various conventional light sources such as an LED (light emitting diode) and a lamp may be used.

Alternatively, pressure pulse wave may be detected by utilizing Doppler shift in the frequency of the light reflected by the presser plate 36, which displaces due to the pressure pulse wave transmitted thereto. The Doppler shift is measured by a well-known photoheterodyne system. In this case it is preferred to use a light source which emits a pair of different laser beams having a pair of different polarization planes orthogonal to each other and a a pair of different frequencies, and a splitter for dividing the mixture laser beams into a first and a second beam. The first beam is reflected by the presser plate 36, and accordingly the optical path of the first beam is changed due to a minute displacement of the displaceable portion 37 of the presser plate 36. The optical path of the second beam is not changed. A first mixture light consisting of the mixture laser beams which have been just emitted by the laser source, is used as a reference light, and a reference beat signal is produced based on the reference light. Meanwhile, a second mixture light consisting of the first beam reflected by the presser plate 36 and the second beam whose optical path is not changed, is used as a measurement light having a shift of beat frequency corresponding to the pressure pulse wave transmitted to the presser plate 36, and a measurement beat signal is produced based on the measurement light. The pressre pulse wave is detected based on the frequency shift of the measurement beat signal from the reference beat signal.

It is to be understood that the present invention may be embodied with various other changes, modifications, and improvements that may occur to those skilled in the art without departing from the scope and spirit of the invention defined in the appended claims.

What is claimed is:

1. A pressure-pulse-wave detecting apparatus for detecting a pressure pulse wave produced from an arterial vessel of a subject, at a plurality of positions on a body surface right above said arterial vessel, the apparatus comprising:

a main body having a pressing surface which is pressed against said body surface, and a plurality of through holes formed therethrough and opening in said pressing surface;

a plate member secured to said pressing surface of said main body such that said plate member covers the openings of said plurality of through holes, said plate member having flexibility and including a plurality of displaceable portions each of which is aligned with the opening of a corresponding one of said plurality of through holes;

a plurality of optical fibers, one of opposite ends of each of said plurality of optical fibers being fitted in a corresponding one of said plurality of through holes of said main body, such that an end face of said one of opposite ends is opposed to a corresponding one of said plurality of displaceable portions of said plate member at a predetermined distance therefrom; and a plurality of signal generating devices each of which is connected to the other of the opposite ends of a corresponding one of said plurality of optical fibers, said each signal generating device detecting the pressure pulse wave transmitted to a corresponding one of said plurality of displaceable portions of said plate member, based on minute displacement of said corresponding displaceable portion which is optically detected through said corresponding optical fiber, and generating an electrical signal representing the detected pressure pulse wave.

2. The apparatus as set forth in claim 1, further comprising:

pressing means for pressing said plate member secured to said pressing surface of said main body, against said body surface, wherein said pressing means comprises:

a cylindrical housing with a bottom wall, for accommodating said main body;

a flexible diaphragm disposed between said housing and said main body, for securing said main body to said housing, said diaphragm cooperating with said housing and said main body to define a fluid-tight pressure chamber;

a band attached to two sides of said housing for holding said housing on said body surface; and a pressure source connected to said pressure chamber, said pressure source supplying pressurized fluid so as to inflate said diaphragm and thereby press said main body against said body surface.

3. The apparatus as set forth in claim 1, wherein said main body has rigidity.

4. The apparatus as set forth in claim 1, wherein said main body has grooves formed in said pressing surface thereof, said grooves being covered by said plate member secured to said pressing surface, said plurality of through holes communicating with the atmosphere via said grooves covered by said plate member.

5. The apparatus as set forth in claim 1, wherein said plurality of through holes are formed through said main body such that the through holes are arranged in a row at regular intervals of distance.

6. The apparatus as set forth in claim 5, wherein each of said regular intervals of distance is about 0.2 mm long.

7. The apparatus as set forth in claim 5, wherein, about 3 to 5 of said regular intervals of distance are equal to the width of said arterial vessel with said main body pressed against said body surface.

8. The apparatus as set forth in claim 1, wherein each of said signal generating devices comprises:

a laser source for emitting laser beams having a single wavelength and an optical path;

a first convex lens disposed along said optical path for forming said laser beams into parallel beams and for transmitting said parallel beams along said optical path;

a non-polar beam splitter disposed along said optical path for dividing said parallel beams into a first and a second beam, such that said beam splitter transmits said first beam along said optical path and reflects said second beam along a second optical path;

a second convex lens disposed along said optical path for permitting said first beam to be incident on an end face of the other of the opposite ends of a corresponding one of said plurality of optical fibers, said first beam being transmitted by said corresponding optical fiber, reflected by a corresponding one of said displaceable portions of said plate member, again transmitted by said corresponding optical fiber, and reflected by said non-polar beam splitter along a third optical path, said first beam having a phase varying due to said minute displacement of said corresponding displaceable portion;

a reflector mirror for reflecting said second beam, said second beam being reflected by said reflector mirror in an opposite direction along said second optical path and transmitted by said non-polar beam splitter along said third optical path, said second beam having a reference phase;

a photosensor disposed across said third optical path for detecting a mixture light consisting of the first beam reflected by said beam splitter and the second beam transmitted through said beam splitter; and a detector circuit for reading a shift in phase between said phase and said reference phase in said mixture light at regular minute intervals of time, and generating said electric signal based on the readings at said regular minute intervals of time.

9. The apparatus as set forth in claim 1, further comprising:

a control device operably connected to said signal generating devices, wherein said control device further comprises:

means for processing the electric signals supplied from said plurality of signal generating devices;

means for selecting one of said electric signals which is free from influences of the wall of said arterial vessel; and means for monitoring blood pressure of said subject based on the selected electric signal.

10. The apparatus as set forth in claim 1, further comprising:

a control device operably connected to said signal generating devices and a pressure source, wherein said control device further comprises:

means for receiving the electric signals from said plurality of signal generating devices;

means for varying the pressing force, based on a control signal between said control device and said pressure source, with which said main body is pressed against said body surface; and means for determining a degree of arterial sclerosis of said arterial vessel based on the received electric signals.

* * * * *